United States Patent [19]

Lacy

[11] Patent Number: 5,741,971
[45] Date of Patent: Apr. 21, 1998

[54] METHOD FOR ANALYZING PHYSICAL PROPERTIES OF MATERIALS

[75] Inventor: Lewis L. Lacy, The Woodlands, Tex.

[73] Assignee: BJ Services Company, Houston, Tex.

[21] Appl. No.: 587,700

[22] Filed: Jan. 17, 1996

[51] Int. Cl.$^6$ ............................................. G01N 29/18
[52] U.S. Cl. ........................ 73/597; 73/32 A; 73/54.41; 73/64.42; 73/152.16
[58] Field of Search ...................... 73/597, 594, 54.03, 73/54.41, 64.42, 32 A, 152.16

[56] References Cited

U.S. PATENT DOCUMENTS

| | | | |
|---|---|---|---|
| 3,316,755 | 5/1967 | Ensley | 73/597 |
| 4,259,868 | 4/1981 | Rao et al. | 73/597 |
| 4,327,587 | 5/1982 | Docekal et al. | 73/597 |
| 4,530,234 | 7/1985 | Cullick et al. | 73/53 |
| 4,616,508 | 10/1986 | Jörn | 73/823 |
| 4,754,645 | 7/1988 | Piche et al. | 73/597 |
| 5,138,585 | 8/1992 | Angehrn et al. | 367/86 |
| 5,214,251 | 5/1993 | Orban et al. | 181/102 |
| 5,276,656 | 1/1994 | Angehrn et al. | 367/86 |
| 5,345,819 | 9/1994 | Dearing, Jr. | 73/153 |

FOREIGN PATENT DOCUMENTS 2 061 508  5/1981  United Kingdom.
2 120 793  12/1983  United Kingdom.

OTHER PUBLICATIONS

Lacy, Lewis, L. and A.C. Daniel, Measurements of Ultrasonic Velocities Using a Digital Averaging Technique. *The Journal of the Acoustical Society of America*, vol. 52, No. 1 (Part 2) (Jul. 1972) pp. 189–195.

Lacy, Lewis L. and Michael Berry Smith, Fracture Azimuth and Geometry Determination. *Recent Advances in Hydraulic Fracturing*, Chapter 16, pp. 341–356.

Warpinski, N.R. and Michael Berry Smith, Rock Mechanics and Fracture Geometry. *Recent Advances in Hydraulic Fracturing*, Chapter 3, pp. 57–80.

*Primary Examiner*—John E. Chapman
*Attorney, Agent, or Firm*—Arnold, White & Durkee

[57] ABSTRACT

An apparatus and method for nondestructively measuring a sample of material to determine changes in dynamic Young's Modulus, density, static viscosity, compressive strength and expansion or contraction of a material over a period of time and at substantially constant temperature and pressure. Samples of particular interest are cements and completions gels whose characteristic dynamic Young's Modulus, density, viscosity, compressive strength and expansion or contraction at down-hole conditions are particularly important to the petroleum industry.

14 Claims, 15 Drawing Sheets

METHOD FOR ANALYZING PHYSICAL PROPERTIES OF MATERIALS

BACKGROUND OF THE INVENTION

Laboratory procedures and instruments that simulate down-hole conditions and measure physical and mechanical properties of materials used in oil and gas recovery operations are important to the petroleum industry because they provide information necessary to accurately schedule drilling and completions operations, as well as, methods to analyze the effectiveness of new additives for drilling and completions procedures. Three particularly important materials that vary in viscosity and density at down-hole temperatures and pressures are cement slurries, hydraulic fracturing gels, and completions gels.

Presently, ultrasonic cement analyzers (UCA) are widely used to test cement compositions before pumping them into oil and gas wells. A UCA is described in U.S. Pat. No. 4,259,868, entitled "Method and Apparatus for Nondestructive Testing of Cement" issued on Apr. 7, 1981 to Rao, et al. UCA's measure ultrasonic transit time through cement samples at a constant temperature and pressure. The primary engineering data provided by a UCA is the time required to achieve a minimum initial compressive strength (i.e., set time) and a maximum compressive strength value. Compressive strength values typically range from about 100 psi to about 3000 psi. The UCA does not provide information regarding cement shrinkage or expansion. The amount of shrinkage in cements at down-hole temperatures and pressures is significant. With a shrinkage of 3 to 5%, good bonding of the cement to the casing and the formation is doubtful and zone isolation is questionable. Cement shrinkage during setting can lead to a poor cement job, poor interzone isolation, and the lack of fracture containment. However, if the degree of shrinkage can be predicted, adjustments may be made to correct for these problems. A single method that demonstrates both compressive strength, and shrinkage or expansion of materials, such as cement, is needed.

Moreover, two critical criteria for the petroleum industry include the time that a gel requires to cross-link or set up and the time required to break the gel so that it may be removed after treating a subterranean formation is completed. Gel cross-linking and breaking times are affected by down-hole temperatures and pressures. Presently, gel cross-linking and breaking times are typically evaluated in the laboratory using a Fann Viscometer, however, the Fann Viscometer does not completely simulate down-hole conditions. Since simulating down-hole conditions is critical to correlating laboratory data with the physical properties of gel at in situ or down-hole conditions, a method for measuring static gel cross-linking and breaking times and static gel viscosity at simulated down-hole conditions is needed.

SUMMARY

The invention may include an apparatus for non-destructively characterizing changes in a material as a function of time, comprising an autoclave subsystem, an ultrasonic subsystem and an electrical subsystem. The autoclave subsystem includes a housing in which at least one wall is movable for decreasing or expanding the volume of the housing to accommodate a contracting or expanding sample of material. The ultrasonic subsystem includes a transmitting transducer adapted to emit a plurality of ultrasonic signals through the material along a length of the housing that may be lengthened or shortened by the movable walls of the housing, a pulser for exciting the transmitting transducer, a transducer adapted to receive the ultrasonic signals, a counter adapted to measure the transit time of the ultrasonic signals, and a micrometer or linear variable differential transducer (LVDT) adapted to measure the length of the housing along which the ultrasonic signal is passed. The electrical subsystem includes a programmed central processing unit having signal conditioning circuitry and adapted to receive and process the length measurements, the transit time measurements and generate a signal that is representative of specific characteristics of the material through which the ultrasonic signal was passed. These specific characteristics include dynamic Young's Modulus, density, static viscosity, compressive strength, and expansion or contraction.

The invention comprises a method for nondestructively analyzing a material comprising maintaining a sample in a housing that may be adjusted to accommodate expansion or contraction of the material, controlling the temperature and pressure of the housing, transmitting ultrasonic signals through the material, measuring and recording the transit time of the ultrasonic signals through the material, and the changes in volume of the material, and using these measurements to determine physical changes in the material.

The invention comprises a method and apparatus for non-destructively characterizing physical changes in a sample of material, particularly, changes in dynamic Young's Modulus, density, viscosity, compressive strength and expansion or contraction of a sample over a period of time and at substantially constant temperature and pressure. The apparatus may be referred to as a Dynamic Modulus Analyzer (DMA). One embodiment may include a method to analyze cement to determine dynamic Young's Modulus, density, viscosity, compressive strength, and sample expansion or contraction, which in turn indicates the time at which cement sets up, the degree of cement slurry thickening and the degree that the cement shrinks or expands under simulated down-hole conditions. The invention may also include a method to analyze a gel strength to determine changes in viscosity, density, dynamic Young's Modulus, and sample expansion or contraction, which in turn provides information regarding changes in the time at which a gel cross-links or sets and changes in the time at which the gel breaks under simulated down-hole conditions.

DETAILED DESCRIPTION OF PREFERRED EMBODIMENTS

The nondestructive apparatus of the present invention is based upon measurement of the travel time of an ultrasonic signal through an expanding or contracting sample of material. A very accurate relationship has been developed for relating the travel time of the ultrasonic signal, the length of the material through which the signal is passed and the change in volume of the material to changes in the material's dynamic Young's Modulus, compressive strength, viscosity, density and expansion or contraction. A technique for measuring the physical changes in samples of materials over a period of time is provided by the apparatus of the present invention.

Figure 1:
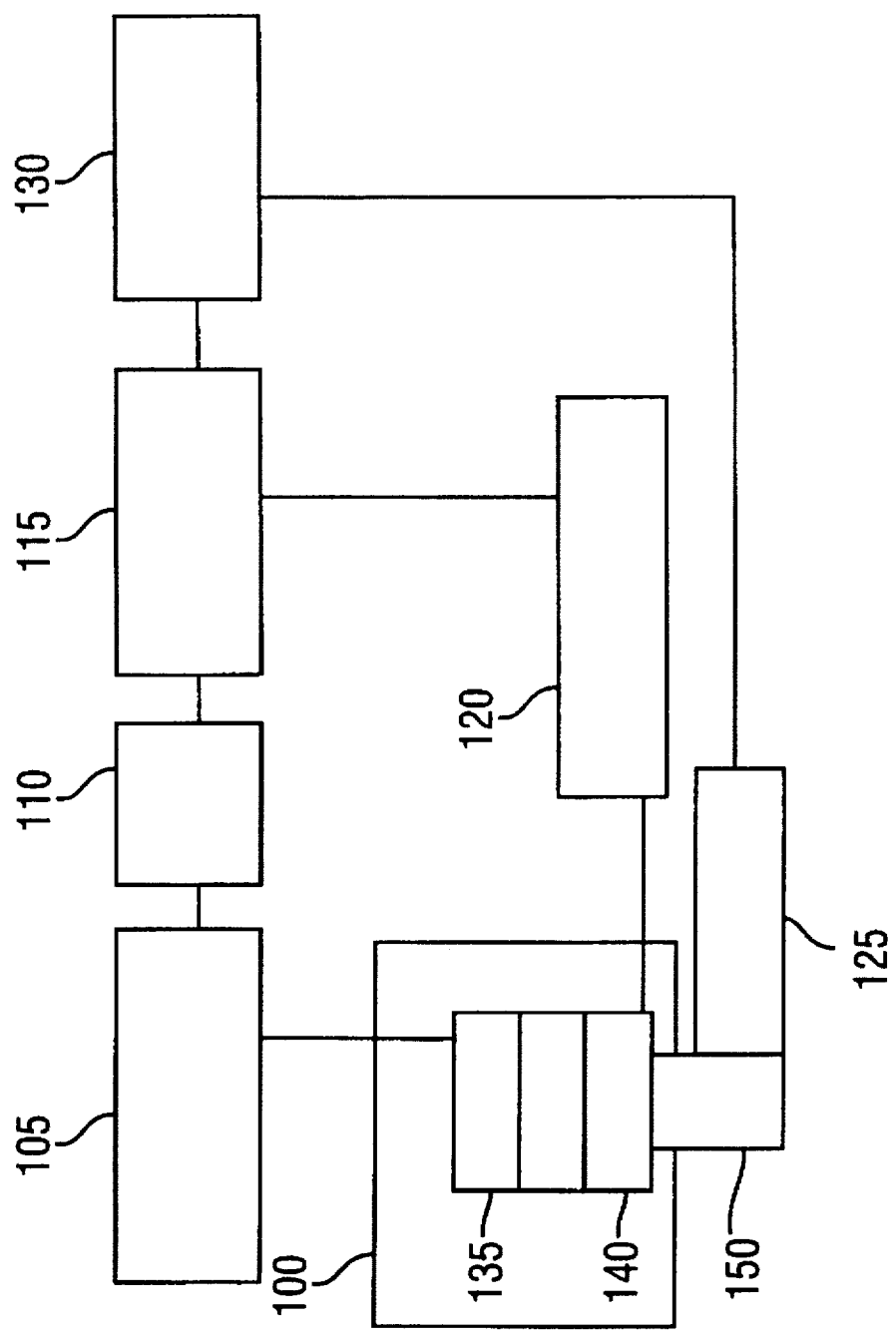
FIG. 1 illustrates a schematic of an embodiment of the apparatus of this invention.
Figure 2:
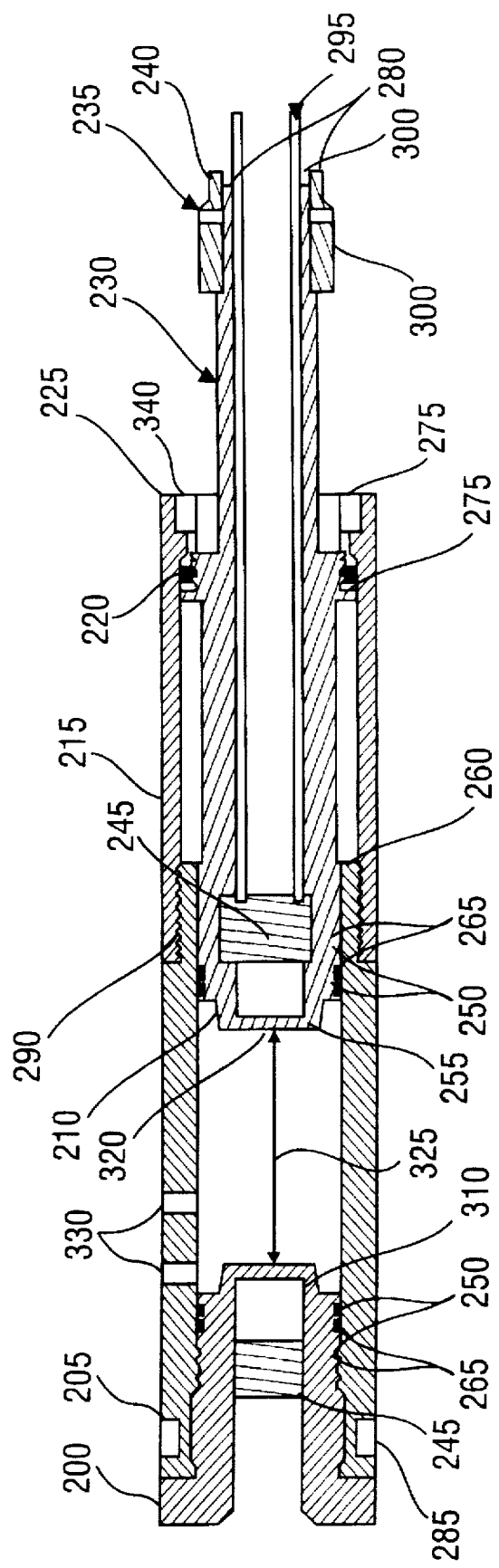
FIG. 2 illustrates an engineering sketch of one embodiment of the autoclave of this invention.

Referring initially to FIGS. 1 and 2, the components of the apparatus of the present invention include a novel design for an autoclave subsystem (100), an ultrasonic pulser subsystem (105), and an electronic subsystem (110–130). The autoclave subsystem may be comprised of a housing having at least one adjustable wall (320). The autoclave (FIG. 2) may accommodate different size samples of material. The movable autoclave wall (320) may lengthen or shorten the autoclave in response to expansion or contraction of a sample. Movement of the autoclave wall (320) may result in a change in the in length (325) of the interior of the autoclave. Thus, the length measurement may be indicative of the amount of sample expansion or contraction. The autoclave may be adapted to maintain the sample at a substantially constant pressure and temperature.

The ultrasonic subsystem (105–120) may be composed of sensors or transducers (255, 310) positioned to transmit (135) and receive (140) ultrasonic signals through the sample substantially parallel to the length of the interior of the autoclave that may be lengthened or shortened by movement of the movable autoclave wall (320). The electronic subsystem (120–130) may measure multiple replications of the transit times of the ultrasonic signals and may measure multiple replications of the changing sample lengths (125) through which the signal passes. The electronic subsystem (120–130) may also comprise a programmable central processing unit (130) adapted to average the multiple replications, and use these figures to calculate dynamic Young's Modulus, compressive strength, density, viscosity and sample expansion or contraction for the sample of material.

An apparatus of this invention may be developed, calibrated and tested on materials, two examples of which include cements and completions gels. This embodiment may be used to evaluate materials and to predict in situ or down-hole properties.

Referring to FIG. 1, the components of a preferred apparatus according to the concept of this invention are illustrated schematically. The components include: an autoclave (100), a transmitting sensor or transducer (135), a receiving sensor or transducer (140), an ultrasonic pulser (105), a digital sync delay (110), a digital counter (115), a general purpose computer (130), a digital micrometer (125), signal conditioning circuitry including low and high pass electronic filters (120) and an amplifier (120).

Autoclave and transducer housing designs of a preferred embodiment are shown in FIG. 2. High strength titanium may be used as a sensor or transducer housing to improve the coupling and transmission of sonic waves into and out of the sample and to protect the transducers from high pressure inside the autoclave. The travel time of sonic waves in titanium (i.e. 4.18 µs/in) may be subtracted from the measured values in the sample.

The length of the sample (325) through which the ultrasonic signal is passed may be measured with a digital micrometer (125). The digital micrometer (125) measures the length of an extension tube (150 and 230) that protrudes from the autoclave. Changes in sample length are measured from the top of the autoclave (275) to the bottom of an extension tube nut (300). The sample of material may be allowed to expand or contract along one length at constant pressure and temperature. The remaining dimensions of the autoclave interior are maintained substantially constant such that the change in length measurement, described above, is indicative of sample expansion or contraction.

The temperature of the sample in a preferred autoclave may be controlled by heater elements, a thermocouple and a temperature controller. Constant pressure may be maintained on the sample by a pressure regulator that regulates the pressure that drives a moving titanium piston (210).

In a preferred embodiment, the piston (210) has two ends. One of the ends is coupled to a gas or fluid pressure container (215) and the other end of the piston comprises a movable wall (320) of the autoclave and may also house the transmitter and/or receiver and their respective housings (200, 210). A transmitter and receiver (255, 310) transducer may be positioned on the same or opposing ends of the autoclave walls or piston end. In a preferred embodiment, the autoclave system may be hydrostatically tested to about 20,000 psi before certification to operate the system up to about 10,000 psi. Even higher operating pressure should be possible with some slight design modifications to the system. An ultrasonic pulser (105) may excite a transmitting piezoelectric (i.e. ultrasonic) transducer that generates or transmits a compressional wave at 0.2 to 4 Mhz through the length of a sample of materials.

The ultrasonic pulser (105) may generate a fast-rise-time pulse of about 400 to 800 V and a synchronization (sync) pulse that begins about 75 ns before the primary pulse. A receiving ultrasonic transducer may detect the ultrasonic waves, which are electronically filtered with low pass (3 MHz) and high pass (0.1 MHz) filters (120) before being amplified (120) with a gain of 45 to 60 dB. The electronic counter (115) may measure the transit time for the ultrasonic wave to an accuracy of about 0.01 µs/in and a sensitivity of about 0.1 ns/in. The purpose of the digital sync delay (110) (delay time equals about 5.158 µs) is to prevent the electronic counter from triggering on the initial pulse, which occasionally interferes with the received signal. The pulser (105) may operate about 500 times per second to generate ultrasonic waves, the transit times of these ultrasonic waves are measured about 100 times to about 1000 times before averaging the results.

The apparatus design may be based upon digital averaging techniques described in L. L. Lacy and A. C. Daniels "Measurement of Ultrasonic Velocity Using a Digital Averaging Technique," Journal of Acoustic Society of America, Vol. 52, 189–199 (1972). In a preferred embodiment about 100 to about 1000 signals were averaged for each determination.

A preferred embodiment of the apparatus of this invention may include an autoclave depicted in FIG. 2 having the following components: a fixed bottom ultrasonic-transducer housing (200) made of titanium or steel; a sample housing (205) adapted for high-temperature and high-pressure testing of materials such as gels or cements; a top piston ultrasonic-transducer housing (210) made of titanium or steel and having an adjustable location; a gas or fluid pressure container (215) adapted for applying pressure to the top piston; o-rings (220–225) that may be contiguous with the piston and the autoclave walls for gas or fluid pressure containment; a piston-extension tube (230) adapted for an ultrasonic transducer housing; a screw-on nut (235); an extension tube adapter (240) for controlling spring tension to ultrasonic transducer; springs (245) coupling the ultrasonic transducers with the sensor housings; o-rings (250) for liquid sample containment; a top ultrasonic transducer (255); a stainless steel retaining screw (260); grooves for o-rings (265–275); a retaining ting (280) made of carbon spring steel; machined holes for an adjustable pen spanner wrench (285); Molykote "U" paste or "L" paste for ss threads (290); a stainless steel ultrasonic-transducer-extension tube (295); grooves on ultrasonic-transducer-extension tube (300); a bottom ultrasonic transducer (310). Two sample housing ports (330) may be used to inject fluid samples or to allow sample access for measuring sample temperature and pressure. One or more pressure ports (340) may be used to provide a gas or liquid at a constant pressure. Heat shrinkable "TEFLON"® tubing may also be used.

Referring to FIG. 1, a preferred embodiment of the apparatus of this invention may include the following commercial components: an ultrasonic pulser (105) with filter and amplifier (120), specifically a Panametric Pulser Receiver Model 5055PR or Panametric HV Pulser Receiver Model 5058PR, commercially available from Panametrics Inc., Waltham, Mass.; a digital counter (115), specifically a Hewlett Packard Model 53131A Universal Counter, commercially available from Hewlett Packard and calibrated to an accuracy of at least 5 ns.; a heater, specifically a Baroid High Pressure and Temperature Filter Press, commercially available from Baroid Testing Company, Houston, Tex.; a temperature controller, specifically a Cole-Palmer Model 2186 Temperature Controller, commercially available from Cole-Palmer Instrument Company, Chicago, Ill.; digital calipers or LVDT, commercially available from Starrett and calibrated to an accuracy of about 0.001 inch; and two high-temperature ultrasonic transducers, (255, 310, 135 and 140) specially ordered from Panametrics Inc. to be one inch in diameter, have a center frequency of 1 MHz, have the capacity for routine operation at 250° F. and have a microdot connector on the back.

A general purpose computer (130) may be used and the software may be operated in a Windows 3.1 or Windows 95 environment using Visual Basic to program the soft-ware. The software automatically sets parameters in the digital counter (115) and starts data acquisition. Data acquisition rates may be selected by the operator and may vary from a one time-average reading per second to a one time-average reading in 30 minutes. A time-average reading consists typically of about 100 real-time readings before averaging the results, but may consist of up to about 1000 real-time readings. This procedure increases the accuracy and sensitivity of the test by averaging out any jitter or electronic noise. Testing may be conducted for about 24 to 50 hours using about 2 to 5 minutes per time-averaged reading.

In a typical sequence of a preferred embodiment, the electronic counter (115) may be programmed to read the peak negative and positive voltage from the receiving sensor (140). The triggers may be programmed to be set at a percent of the peak voltage. The operator may select, through the software, the percent value for each trigger. In a preferred embodiment, the sync-signal trigger may be set at about 95%, and the first-arrival trigger may be selected at about 40%. The first-arrival trigger may be selected between about 10% and 60%. Transit time data may then be determined at the selected trigger levels (i.e. both positive and negative triggers). The ultrasonic transit time, the sample length, the dynamic modulus and compressive strength may be calculated and stored to file. Both the transit time per unit sample length and dynamic modulus data may be plotted on a general purpose computer screen as a function of time.

The design requirements for a preferred embodiment of the apparatus include a variable sample length of from about 0.5 to about 4 inches, a pressure range of about 0 to about 10,000 psi, a temperature range of about 80° to about 350° F., a transit time accuracy of about 0.01 µs/in which is about 10 ns/in and also about 0.1%, a dynamic modulus accuracy of about 1% and a sample length accuracy of about 0.1%.

A preferred embodiment of the apparatus may accurately measure changes in the dynamic modulus ($E_d$) or sample density ($\rho$) by measuring ultrasonic velocity and the length of the sample through which the ultrasonic signal passes. The ultrasonic compressional wave velocity, $V_c$, is related to changes in the dynamic modulus or sample density by the equation:

$$V_c = \sqrt{\frac{F(v)E_d}{\rho}} \tag{1a}$$

and $$F(v) = \frac{(1+v)(1-2v)}{(1-v)} \text{ solids} \tag{1b}$$

where $v$ is Poisson's ratio for solids. Poisson's ratio was determined for various cement cubes with an average value being $v=0.279$. An average value of $F(v)$ for cements was measured to be 0.784.

Since $V_c$ may be measured with good accuracy (i.e. 0.1%) and high sensitivity (i.e. one part per million change in $V_c$), changes in $E_d$ or $\rho$ may be determined as liquid samples change phases. In the preferred embodiment of the apparatus, both $V_c$ and $\rho$ are monitored separately. Ultrasonic transit time may be monitored by an accurate digital counter, model 53131 A from Hewlett Packard, with an accuracy of 1 ns, and sample length (L) is measured independently with an accurate digital micrometer or linear variable differential transducer (LVDT) with an accuracy of 0.001 inches. Thus changes in the ultrasonic velocity and sample density or shrinkage may be determined along with changes in $E_d$. Changes in sample density ($\Delta\rho$) may be related to changes in sample length ($\Delta L$):

$$\rho = \frac{M}{V} = \frac{M}{\pi L R^2} \tag{2}$$

$$\Delta\rho/\rho_0 = -\Delta L/L_0,$$

for a sample of Mass (M) and sample of volume (V) contained in an autoclave with inner radius (R). One embodiment of this invention may include a sample housing having a fixed volume, which would provide a constant sample length L and a ΔL of zero.

Figure 4:
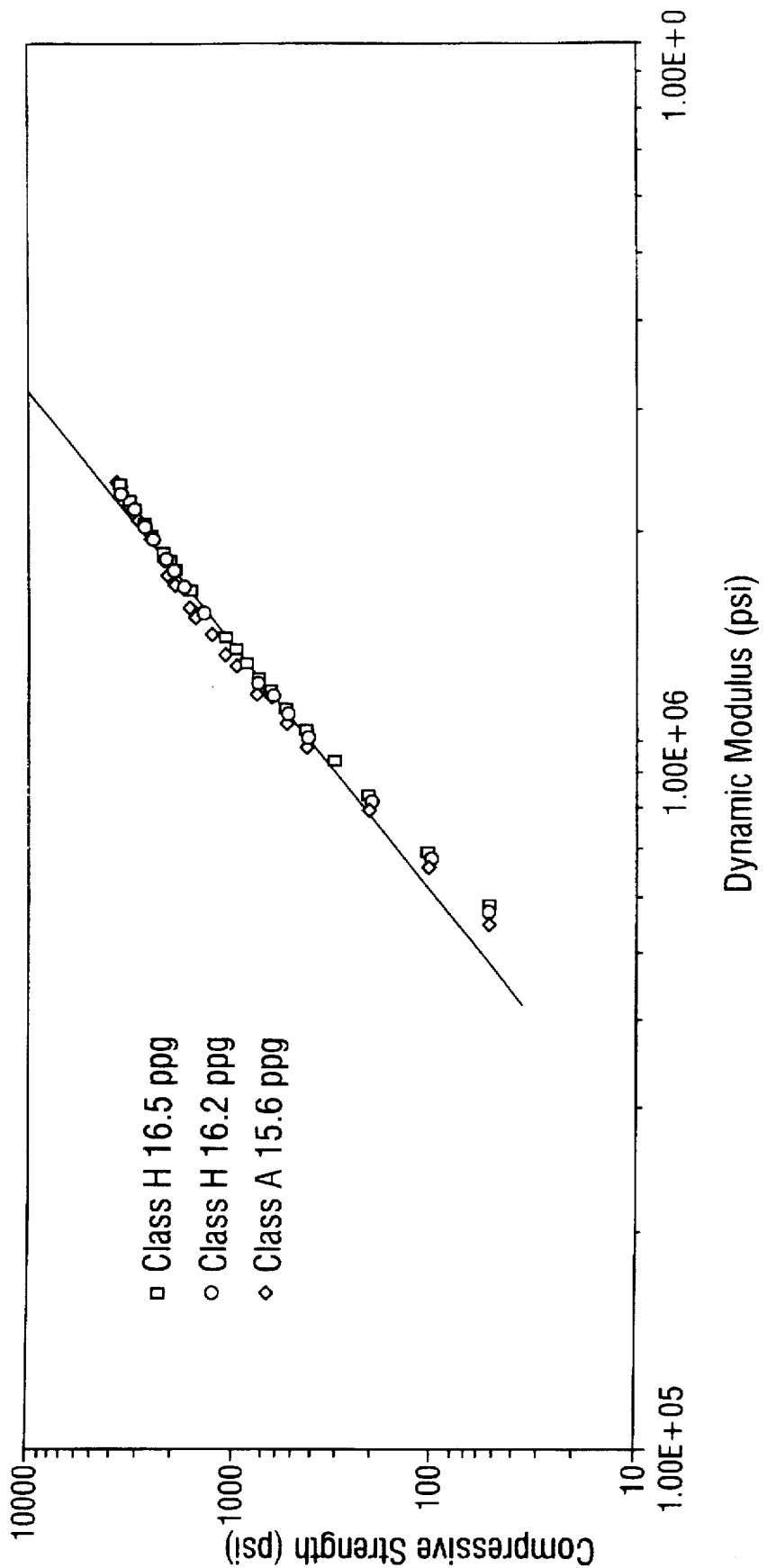
FIG. 4 illustrates analysis of compressive strength versus dynamic modulus for three cements.

Compressive Strength ($C_s$) is related to Elastic Modulus ($E_d$) for cements. Unconfined compressive strength increases with the elastic modulus because all cement test samples fracture or fail by the same mechanism (i.e. compressive failure) at a constant strain of about 1.5%. The data presented in FIG. 4 indicate that $C_s$ may be calculated from $E_d$ data.

Since cements are used in petroleum engineering environments at high confining pressures, the unconfined compressive strength does not correspond exactly to the failure strength of cements. The true failure strength of cements can only be determined in triaxial test chambers. Consequently, the unconfined compressive strength of cements is only a quality control number that may be related to failure strength of cements at high confining pressures. The dynamic Young's Modulus of cement may also be related to the failure strength of cement as a quality control number. The dynamic Young's Modulus of cement may be related to unconfined compressive strength by equation 3.

$$C_s = C_0 E_d^n \quad (3)$$

in which n=2.71 and $C_0$=361 when $E_d$ is measured in Mpsi units (1 Mpsi=1×10$^6$ psi). $E_d$ may be calculated from ultrasonic transit time (t) by the equation:

$$E_d = 13,620 \rho_{ppg} \left( \frac{25.4}{t} \right)^2 \quad (4)$$

in which $\rho_{ppg}$ is the slurry density expressed in pounds per gallon and transit time (t) expressed in μs/in. The velocity of sound in the sample (units cm/s) is the reciprocal of the transit time $$V_c = 2.5 \times 10^6 / t \quad (5)$$

Compressive strength may be calculated by using the equation:

$$C_s = C_0 \exp(-mt)$$

in which $C_0$ and m depend on cement density class as given in Table I.

TABLE I

| Values for $C_0$ and m versus cement density. | | | |
|---|---|---|---|
| SLURRY | CEMENT CLASS | $C_0$ (kpsi) | m(in/μs) |
| Lightweight (<14 ppg) | 1 | 494 | 0.567 |
| Standard (14–16.4 ppg) | 2 | 210 | 0.53 |
| High Density (>16.5 ppg) | 3 | 390 | 0.62 |

In a preferred embodiment, equation 6 may be used to calculate compressive strength for transit times between 5 and 15.5 μs/in. For transit times greater than 15.5 μs/in, the slurry is usually a liquid in which compressive strength is set by the software equal to 1 psi. Class 3 high density cements contain Hematite.

Compressive strength may also be calculated by Equation 3 using the measured dynamic Young's Modulus values. For pure water at room temperature (77° F.) the transit time is 16.96 μs/in. The dynamic modulus for pure water is 0.25×10$^6$ psi. For cement slurries, typical dynamic moduli values are 0.50×10$^6$ psi. When cements set, the dynamic moduli values will increase to 0.6×10$^6$ psi and higher values.

The apparatus of this invention is an improvement over the UCA because the UCA only determines set time and unconfined compressive strength of cement, whereas an embodiment of the invention may be used to determine dynamic Young's Modulus, density, static viscosity and sample expansion or shrinkage as well as compressive strength. In particular, since an embodiment of this invention may be capable of measuring compressive strength at the same time as measuring the expansion or shrinkage of a cement sample, it is an improvement over the UCA. Embodiments of the invention are more accurate than the UCA because they use digital average techniques to correct for inaccuracies that are inherent in ultrasonic analyses. The apparatus of this invention also operates at a higher frequency than the UCA, which along with its ability to measure density as well as viscosity accounts for the capability of the apparatus to analyze gel, as well as, cement samples.

EXAMPLE 1

CALIBRATION

An embodiment of the apparatus of this invention measured the ultrasonic velocity or transit time to an accuracy of 0.01 μs/in and a sensitivity of 0.1 ns/in. An HP digital counter was calibrated by the manufacturer to an accuracy of about 0.5 ns. The digital calipers were calibrated to an accuracy of about 0.001 inch. The velocity of sound in hot distilled water was used to calibrate the apparatus. Published values for ultrasonic velocity in hot water may be found in references such as the AMERICAN INSTITUTE OF PHYSICS HANDBOOK, Third Edition, Chapters 2 & 3, McGraw-Hill Book Company, New York (1972) or the HANDBOOK OF PHYSICS AND CHEMISTRY, 51 St. Edition, The Chemical Rubber Company, Cleveland, Ohio (1971).

Figure 3:
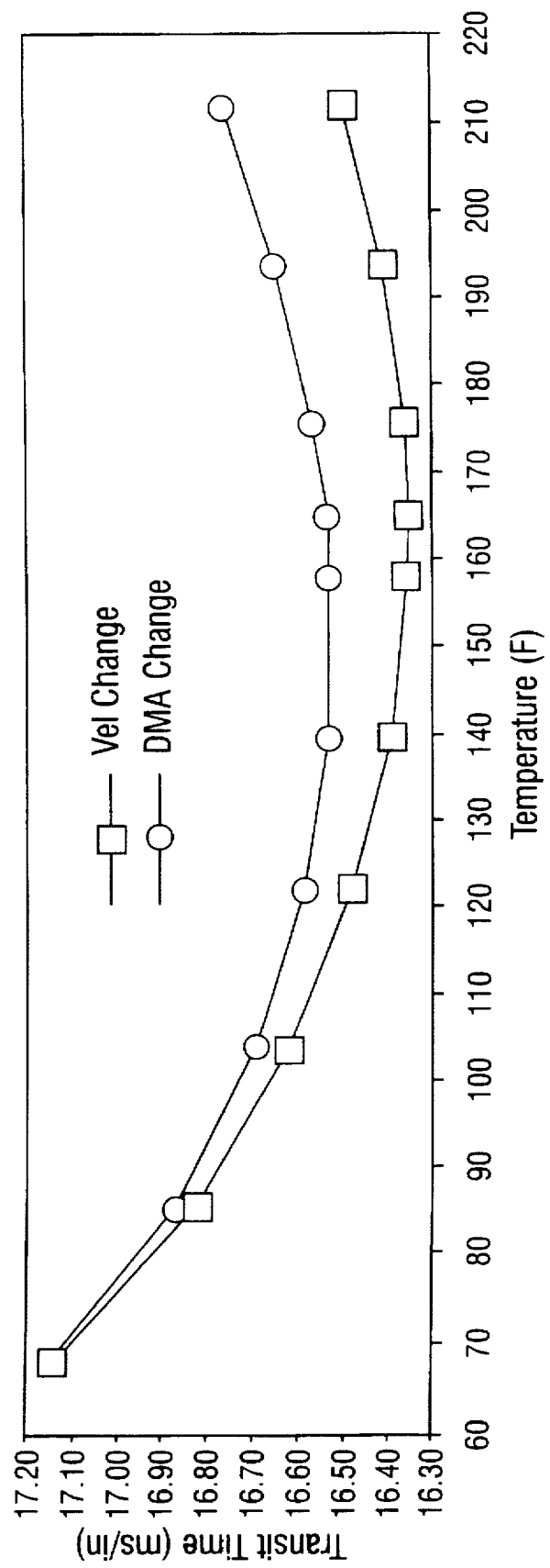
FIG. 3 illustrates calibration test data using distilled water.

Calibration data using hot water are shown in FIG. 3 where transit time is plotted versus water temperature. Two curves are drawn versus temperature in FIG. 3. The Vel-Change curve corresponds to the true change in velocity of sound versus temperature in which the sample length was measured at each temperature. The DMA-Change curve corresponds to changes in which sample length at room temperature is used during the test. At room temperature, both curves converge. It is noteworthy in FIG. 3 that most of the transit time change occurs because of velocity changes and not sample length changes.

Since the attenuation of sound in water is very small, the length of the sample through which the ultrasonic signal is passed is not critical and can be selected anywhere from about 0.5 to about 4.0 inches. Ultrasonic sound waves at 1 MHz can travel 175 feet in water before any significant attenuation. Likewise ultrasonic attenuation in most set cements is low. The highest ultrasonic attenuation occurs in gels with gel strength exceeding 2×10$^6$ cp. The sample length or volume can be reduced to enhance the ultrasonic signal in materials with high ultrasonic attenuation.

EXAMPLE 2

COMPRESSIVE STRENGTH AND DYNAMIC YOUNG'S MODULUS

The unconfined compressive strength of three cement samples (i.e., class H cement 16.5 ppg, Class H cement 16.2 ppg and class A cement 15.6 ppg) were tested in a preferred embodiment of this invention. For each test, the dynamic Young's modulus of the cement samples were measured simultaneously with the compressive strength measurements. The results are plotted in FIG. 4.

During the cement setting process, the dynamic Young's modulus increased from $0.55 \times 10^6$ psi to $2.5 \times 10^6$ psi. The compressive strength of the cements samples increased from 50 psi to 3500 psi. The data in FIG. 4 demonstrate the close correlation of cement compressive strength to cement Young's Modulus. This correlation between compressive strength (CS) and dynamic modulus (Ed) is expressed by equation 3.

EXAMPLE 3

API Class H cement with 0.1% retarder and a density of 16.2 ppg was cured at a temperature of 200° F. and a pressure of 1000 psi. Cement samples were analyzed using the apparatus of an embodiment of this invention, a UCA, and a curing chamber.

Figure 5:
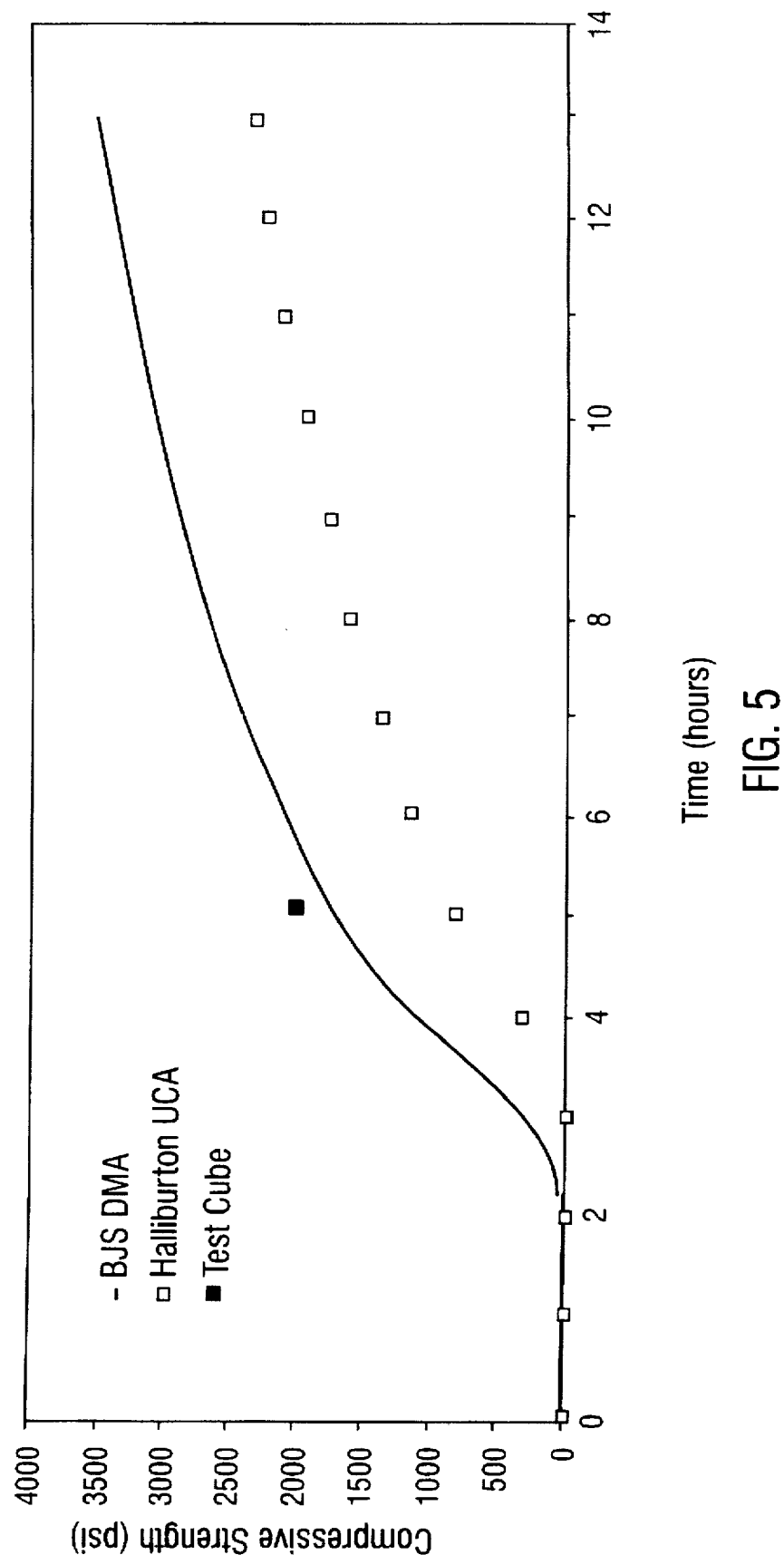
FIG. 5 illustrates a comparison of compressive strength tests for an API Class H cement containing a retarder in a UCA, an embodiment of this invention and a curing chamber at 100° F. and 1000 psi.

FIG. 5 shows the differences in the results between analyses with the UCA and the apparatus of this invention as compared to tests in the curing chamber. Differences are demonstrated in the results for compressive strength for the first 4 hours of curing (i.e. up to the CS=500 psi). After the initial cure and solidification of the Class H cement, the present invention's results show a higher compressive strength than the UCA results. A test cube from the curing chamber was tested after 5 hours and indicated a CS value of 2000 psi, which was closer to the value predicted by this invention than the value predicted by the UCA.

The reason that results predicted by this apparatus correlated more closely with the curing chamber test is believed to be associated with cement shrinkage of Class H cements during curing. When the cement shrinks, free water stands in the UCA test apparatus. The free water has a slower transit time than the set cement, thus slowing down the ultrasonic travel time and causing the UCA result to show a lower compressive strength. In comparison, the design of the preferred embodiment of the invention does not allow free water to form as the cement shrinks because the novel piston design forces the free water away from the titanium housing containing the ultrasonic transducers. Thus, the results of this invention were not affected by the cement shrinkage and the apparatus predicted a higher compressive strength that correlated more closely with curing chamber results.

EXAMPLE 4

MEASURING CEMENT SHRINKAGE

Figure 6:
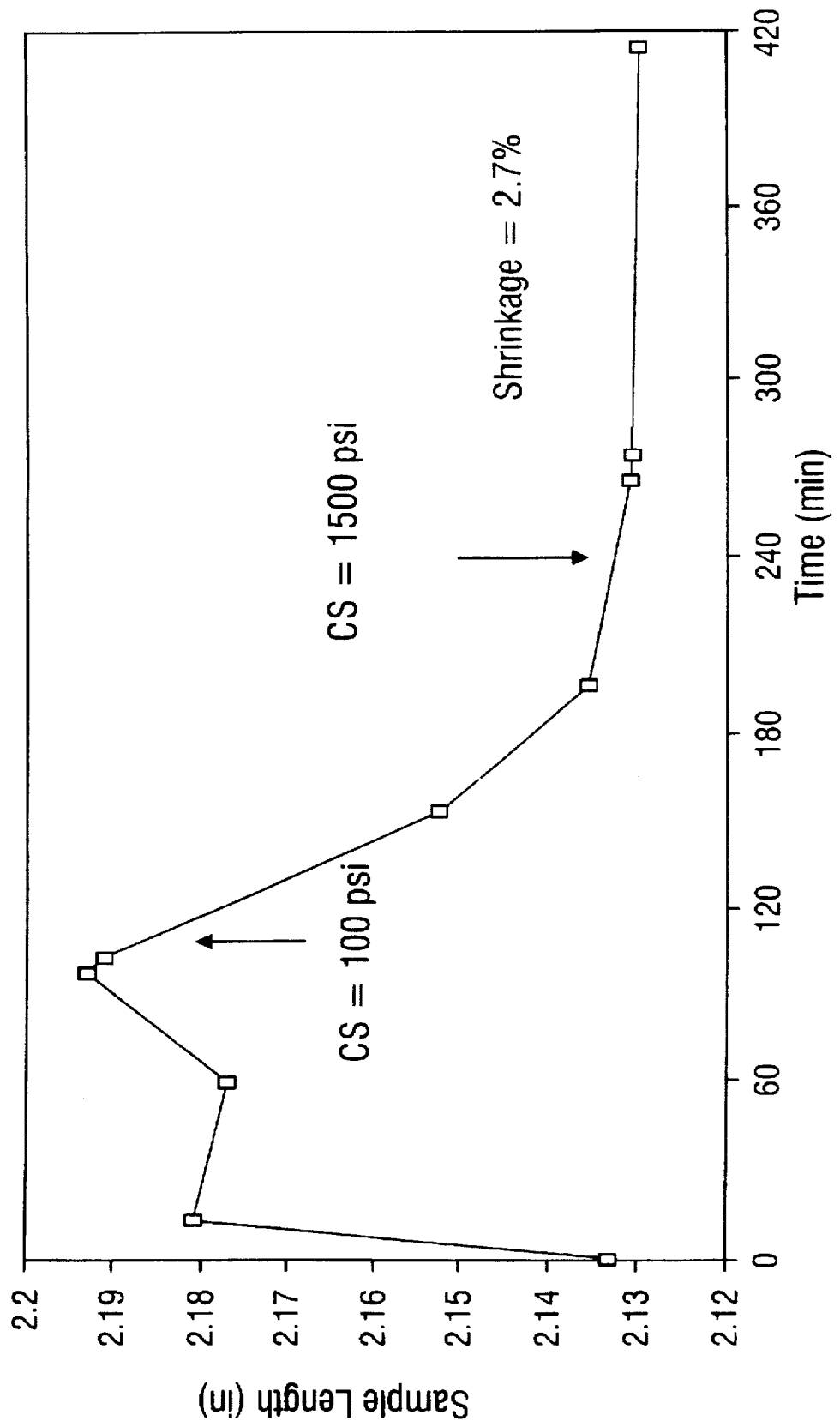
FIG. 6 illustrates determinations of cement shrinkage for an API Class H cement samples.

Cement shrinkage and compressive strength were measured with a preferred embodiment of this invention and the results are shown in FIG. 6 as sample length versus curing time. The initial expansion of the cement slurry in the first 20 minutes of curing was caused by expansion due to the liquid slurry heating up to 240° F. After solidification, the sample began a large contraction or shrinkage (i.e. 2.7%) which lasted approximately 2.5 hours while the sample increased compressive strength from 100 psi to 1500 psi. There was only a small amount of additional shrinkage as the sample's compressive strength increased to 3500 psi. Thus most of the shrinkage took place in the first 1500 psi of change in compressive strength at substantially constant temperature and pressure conditions. Measuring compressive strength while also measuring sample expansion or contraction is a novel use of an embodiment of this invention and an improvement over the conventional UCA method.

EXAMPLE 5

COMPARING UCA AND A PREFERRED EMBODIMENT OF THIS INVENTION TESTS FOR CEMENT SAMPLES

A second Class H cement was tested in the UCA, a preferred embodiment of this invention and a curing chamber test. The cement selected for testing was 16.47 ppg API class H cement without any additives. The results of the tests are plotted in FIG. 7 for a curing temperature of 240° F. and a pressure of 1500 psi. Both the preferred embodiment of this invention and UCA predicted the same initial set time for 500 psi of compressive strength (i.e. 2.5 hours)

Figure 7:
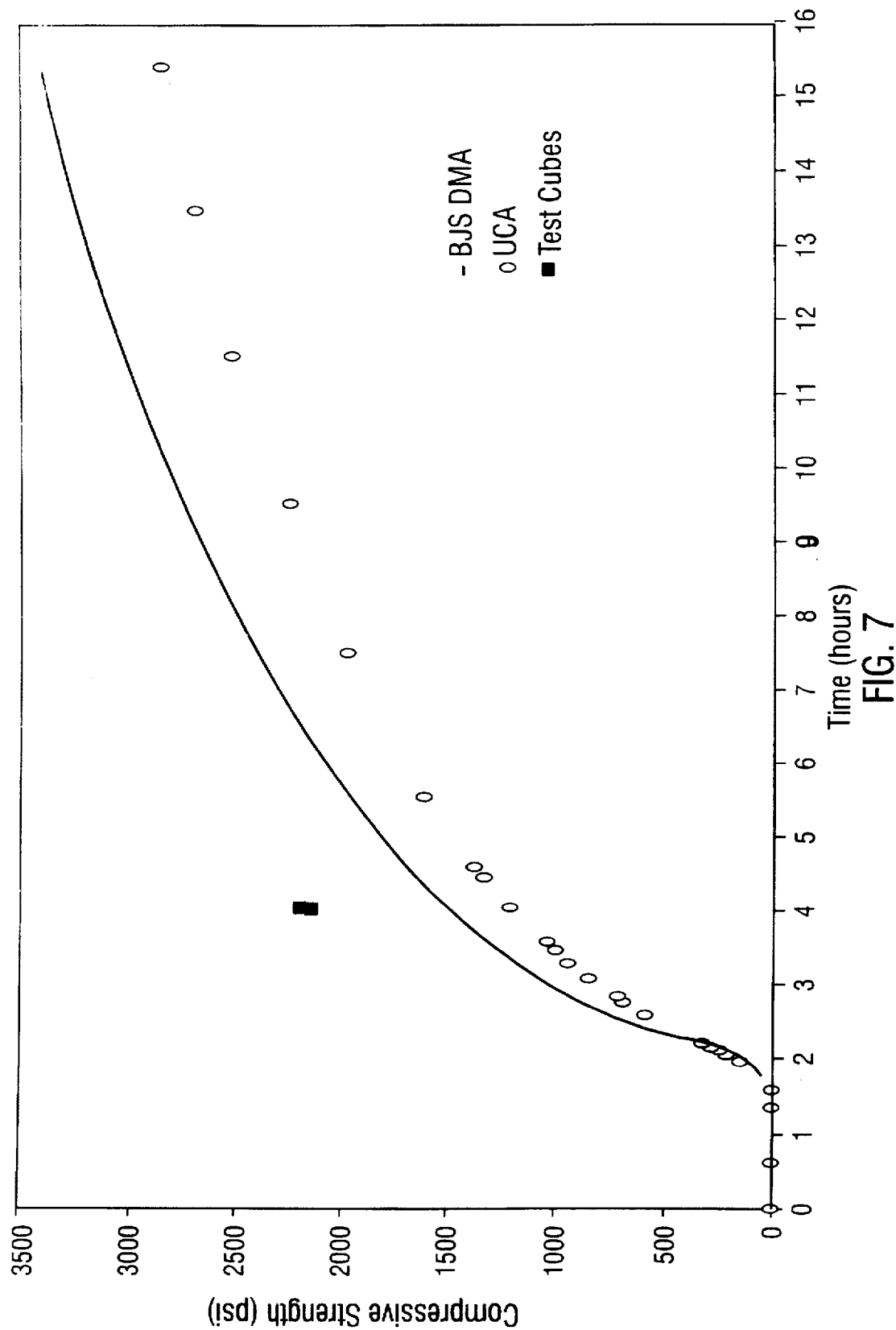
FIG. 7 illustrates a comparison of compressive strength tests for a curing temperature of 240° F. and a pressure of 1500 psi.
Figure 8:
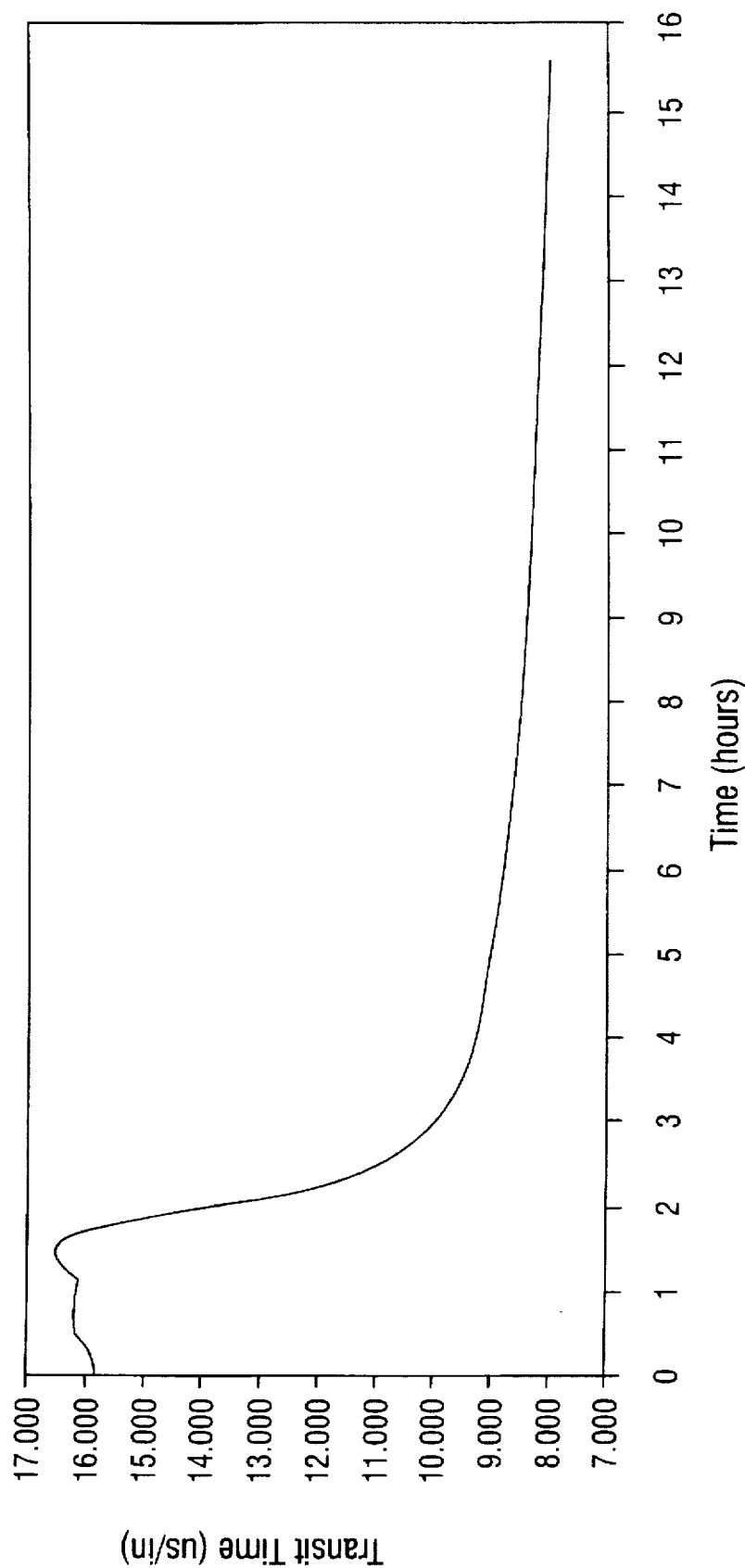
FIG. 8 illustrates ultrasonic transit time measurements in a Class H cement.

The data from an embodiment of this invention presented in FIG. 7 indicated a faster increase in compressive strength than the UCA data after 2.5 hours, but the results from the apparatus correlated better with the compressive strength test of the curing chamber samples than did the UCA. As explained in Example 3, results from the apparatus improved accuracy over the UCA may be associated with the capacity of the apparatus to adjust for cement shrinkage. After 4 hours in a curing chamber, two cement cubes were tested for compressive strength. As previously found, the data from the apparatus gave results more consistent with the curing chamber test, but still under-predicted the compressive strength test results as compared to the cube test. FIG. 8 plots the transit data from the apparatus as a function of setting time.

The data in FIG. 8 indicates that the transit time increases from 16.0 µs/in to 16.2 µs/in as the slurry heats up to 240 F, and after 1.5 hours increases to 16.5 µs/in as the sample sets or gels. The cement has a rapidly decreasing transit time after 1.8 hours at which time the sample hardens and builds strength.

Figure 9:
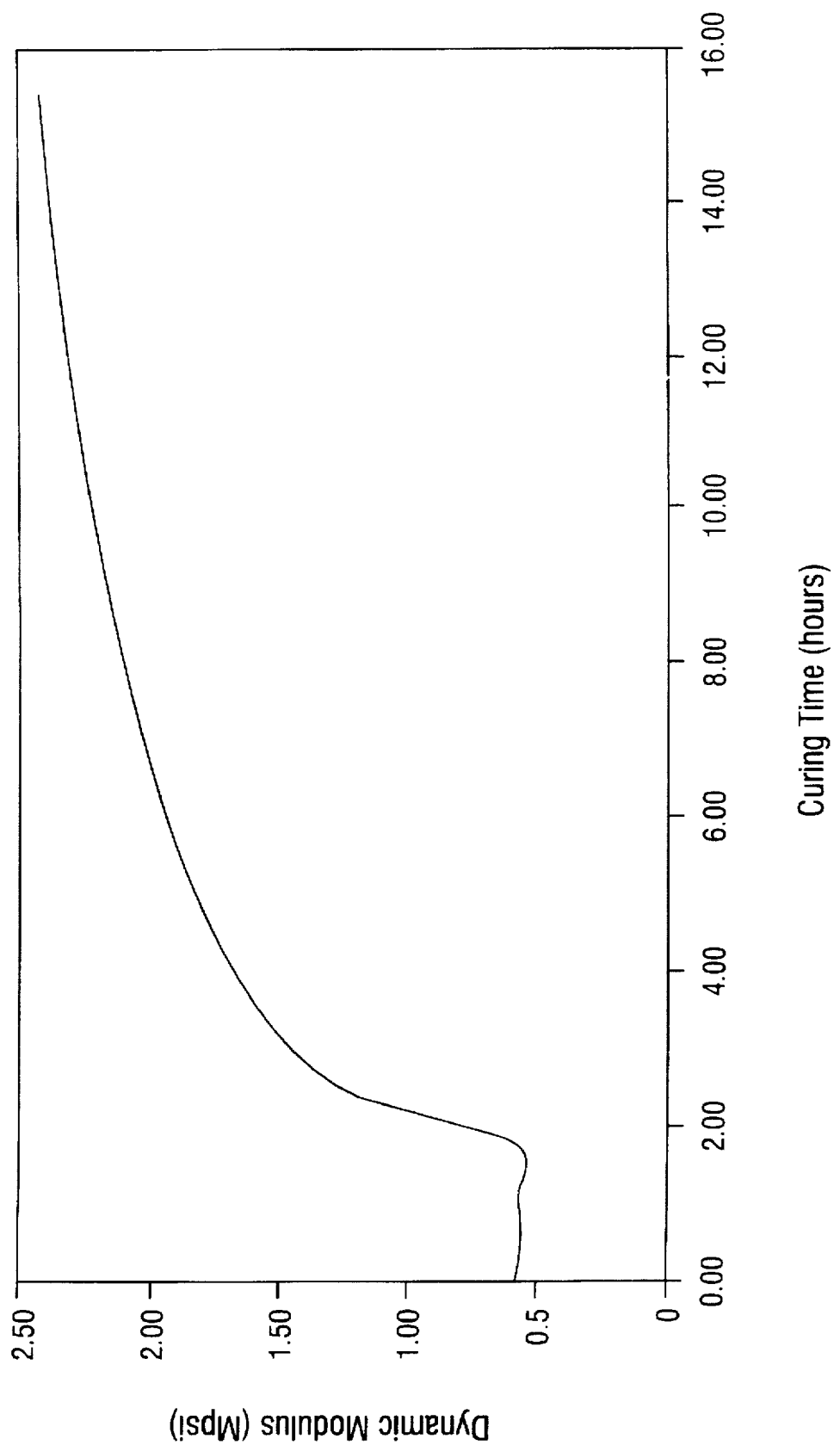
FIG. 9 illustrates analysis of dynamic modulus of Class H cement samples during solidification.

The dynamic modulus (i.e., Young's modulus) of the cement sample was rapidly increasing during this time span as illustrated in FIG. 9. The dynamic modulus of API class H cements increased dramatically during the first few hours after setting as demonstrated in FIG. 9. For cement slurries, the Young's moduli are typically between $0.4 \times 10^6$ and $0.6 \times 10^6$ psi. For set cements, the Young's modulus increased from $0.6 \times 10^6$ psi to $2.5 \times 10^6$ psi in several hours.

Figure 10:
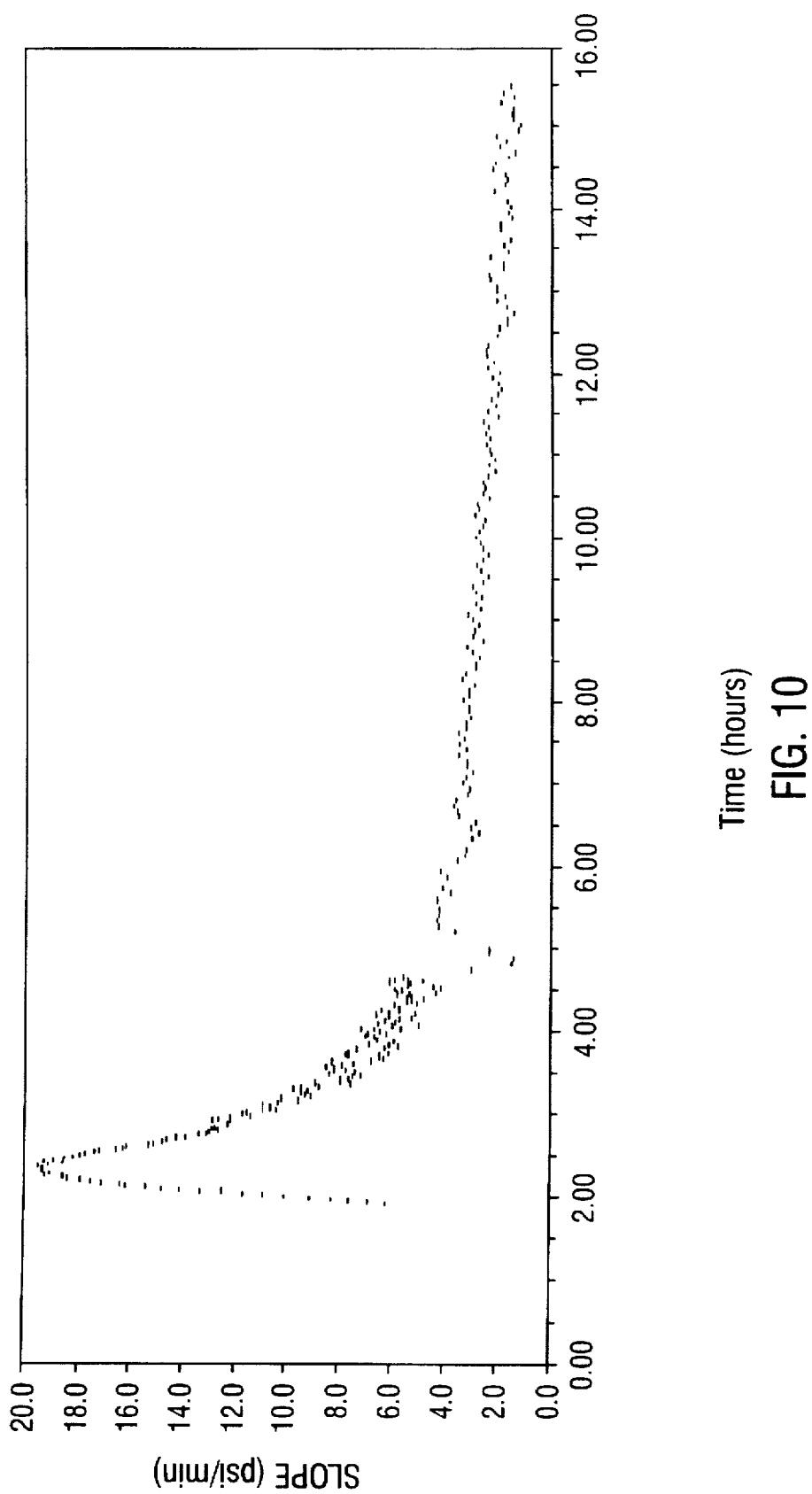
FIG. 10 illustrates analysis of the rate of increase in compressive strength versus cement curing time.

In FIG. 10, the rate of increase of compressive strength is plotted in units of psi/min for the class H cement. The maximum rate of strength increase occurred after 2.5 hours with the maximum rate of 19.0 psi/min. After 6 hours, the rate of strength increase decreased to only 4.0 psi/min. This curve may be used to predict the compressive strength of cements at 24 hours after recording data for only 8 to 12 hours. The compressive strength of this cement sample will increase by only 1440 psi in the next 12 hours after achieving 3100 psi in the first 12 hours. By reducing the test time from 24 to 12 hours or perhaps 8 hours, additional samples may be tested with the apparatus, thus increasing the efficiency of a testing program.

EXAMPLE 6

ANALYZING GEL STRENGTH AND VISCOSITY

Cross-linking gels will increase the gel viscosity from about 1 cp to about 500 cp or greater. Some gels can increase viscosity up to several million cp. As the gel strength increases, the sonic transit time is increased. Likewise, as gels change to higher viscosity states, gel density can change by several percent. Both of these effects will influence the sonic transit time through the gel. The combined effect can be calculated using Equation 7 to determining the fractional change in transit time ($\Delta t/t_0$):

$$\frac{\Delta t}{t_0} = -\frac{\Delta \rho}{\rho_0} - \frac{2}{3} \left[ \frac{\omega \eta}{\rho_0 V_0^2} \right]^2 \quad (7)$$

where $\omega=2\pi f$ is the angular ultrasonic frequency, and $\eta$ the static viscosity of the fluid. The static viscosity of the fluid corresponds to the fluid viscosity at low shear rates for Neutonian or non-Neutonian gels.

The dynamic modulus or $E_d$ of the original fluid before cross-linking or other phase changes occur may be calculated by $E_d = \rho_0 V_0^2$ where $V_0$ is the initial sonic velocity of the fluid. According to Equation 7, DMA's having higher ultrasonic frequencies (f=1 MHz) are more sensitive to detecting viscosity changes. The preferred embodiment of the apparatus detects both density and viscosity changes because it operates at a high frequency, thus the apparatus is sensitive enough for gel analysis.

The cross-linking time depends on temperature and pressure. Likewise, after a proppant has been placed in a fracture, the time required to break the gel is an important parameter when evaluating gel breakers. Two gels were tested using the apparatus and one of the gels was also tested in a UCA. Unlike UCA testing, the DMA apparatus was successful in evaluating the static viscosity or low-shear viscosity (i.e. non-Neutonian) of non-linear gels at high temperatures and pressures.

Figure 11:
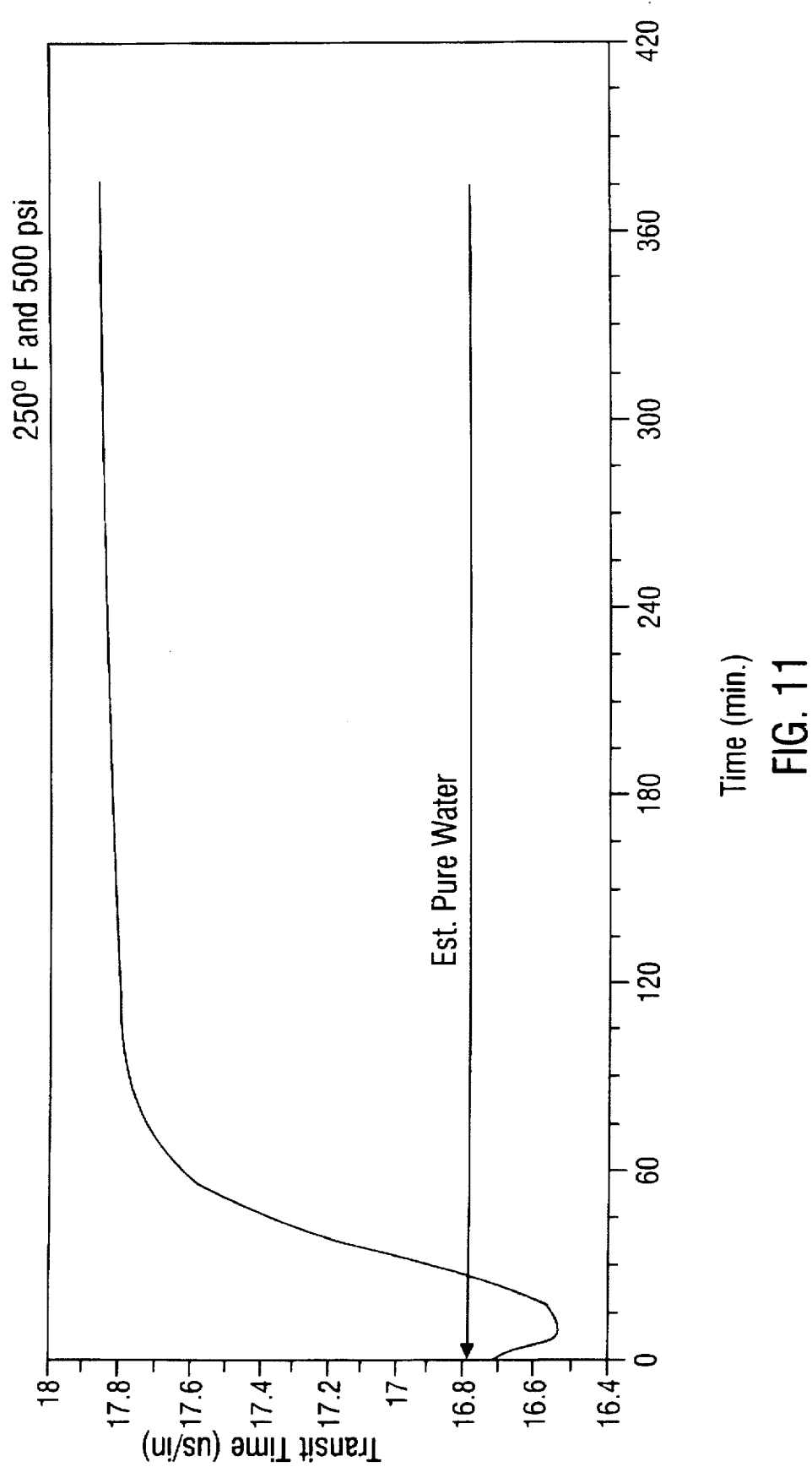
FIG. 11 illustrates sonic transit time measured in a sample of "MEDALLION FRAC"®.

In FIG. 11, sonic transit time was plotted versus time for a "MEDALLION FRAC"® sample that included a delayed cross-linker. The sample was maintained at a temperature of 250° F. and a pressure at 500 psi. The estimated value for distilled water that is shown is based upon an extrapolation of published data. The difference in transit time between the pure water and the "MEDALLION FRAC"® sample is primarily associated with the static viscosity of the gel. A similar test was performed with a UCA in which the UCA results indicated a lack of sensitivity to detect cross-linking and changes in static gel viscosity.

Figure 12:
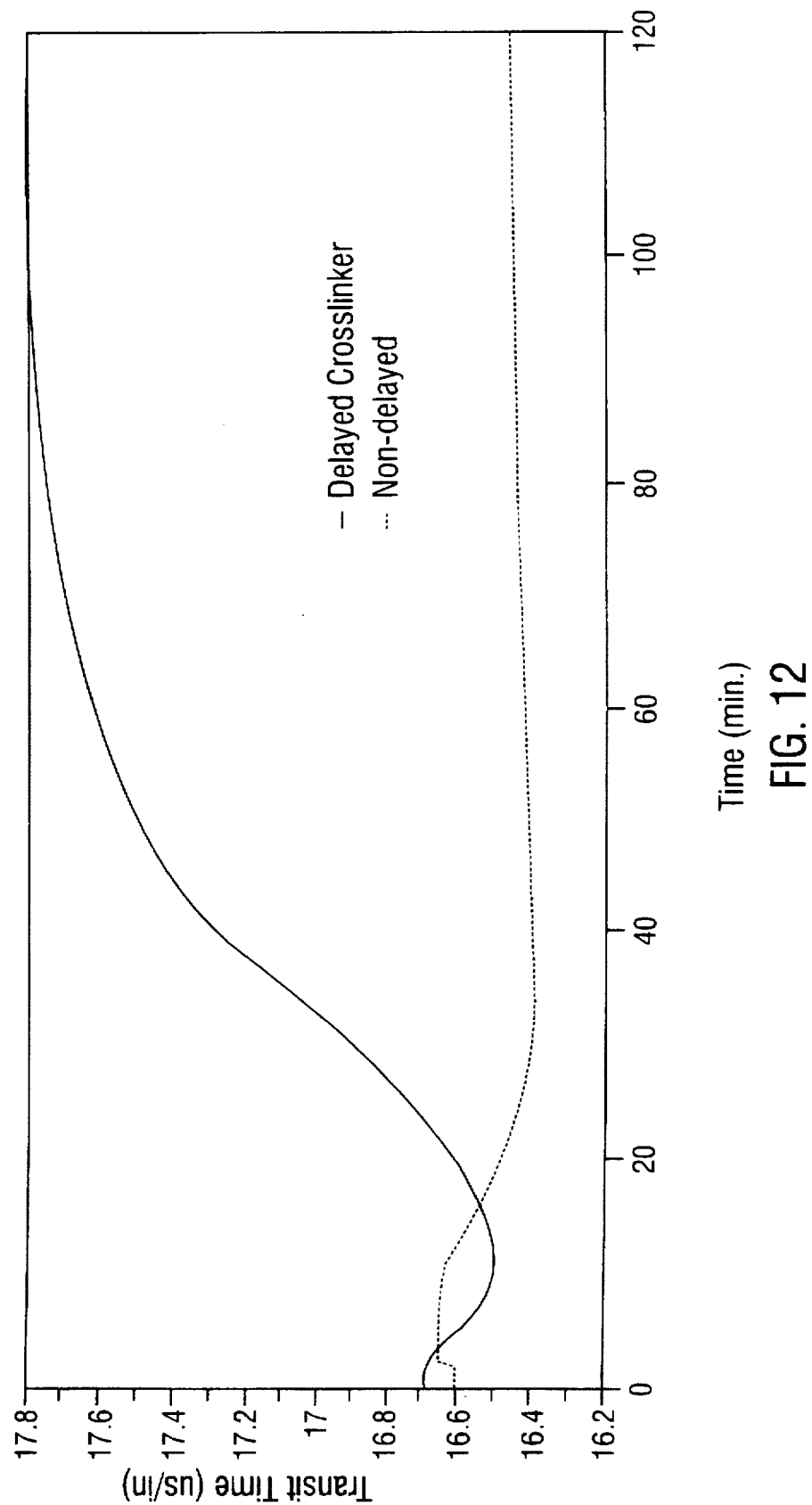
FIG. 12 illustrates sonic transit time for two "MEDALLION FRAC"® gels.

In FIG. 12, two "MEDALLION FRAC"® data sets are plotted. The second data set included higher breaker concentrations than the first data set. The data in the second tests indicated that the gel broke within 40 minutes. The differences in transit times after 100 minutes represents the sensitivity of the apparatus of this invention to measure viscosity changes.

The gelled fluid had a transit time of 17.8 μs/in versus a transit time of 16.4 μs/in for the gel after breaking. Since the broken gel had a viscosity similar to water, the 1.4 μs/in difference between the two values corresponds to about 500 cp change in viscosity. FIGS. 11 and 12 demonstrate that the apparatus is sensitive to changes in gel viscosity or gel strength. Consequently, the apparatus can be used to evaluate gels or fracturing fluids of interest to the petroleum industry.

EXAMPLE 7

GEL CROSS-LINKING AND BREAKING BASED ON DMA STATIC VISCOSITY ANALYSIS

Figure 14:
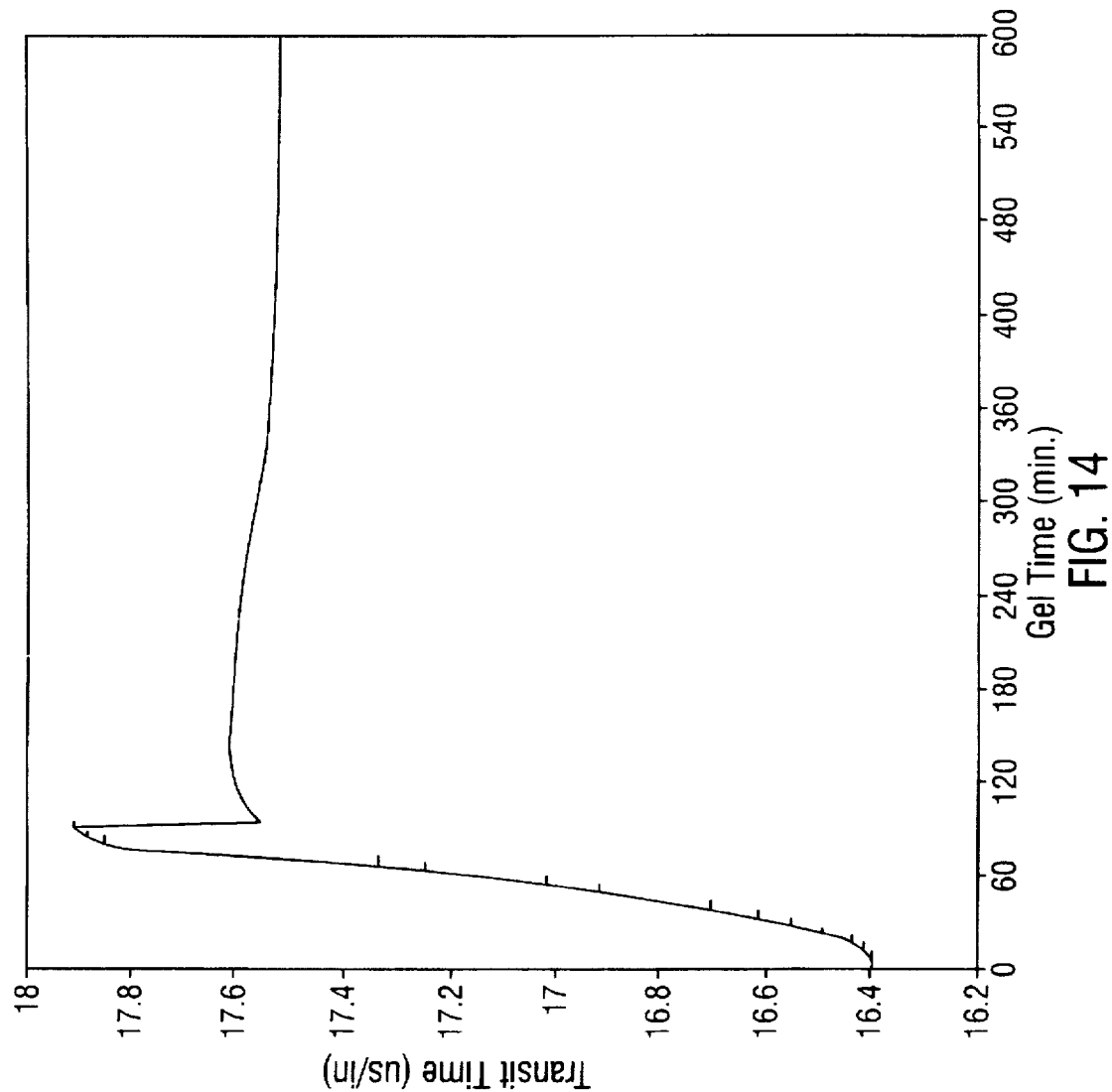
FIG. 14 illustrates analysis of the static viscosity of a gel reported as centipoise (cp) versus gel time in minutes.

Example 7 further demonstrates the clarity with which the degree of gel cross-linking and breaking may be demonstrated with an embodiment of this invention. FIG. 14 demonstrates analysis of the ultrasonic transit time of a fracturing fluid for a gel with increasing strength. The results were plotted as sonic transit time in units of μs/in versus gel time (e.g., cross-linking time) in minutes. The data indicated a definite increase in transit time at 50 up to 80 minutes and then a dramatic break from 80 minutes to 85 minutes. The transit time increased from 16.4 μs/in to 17.9 μs/in as the gel cross-linked and increased gel strength. The rapid decrease in transit time after achieving maximum gel strength is associated with the gel breaking by using a commercial gel breaker.

EXAMPLE 8

GEL CROSS-LINKING AND BREAKING DETERMINATION BASED ON DMA ULTRASONIC TRANSIT TIME ANALYSIS

Figure 13:
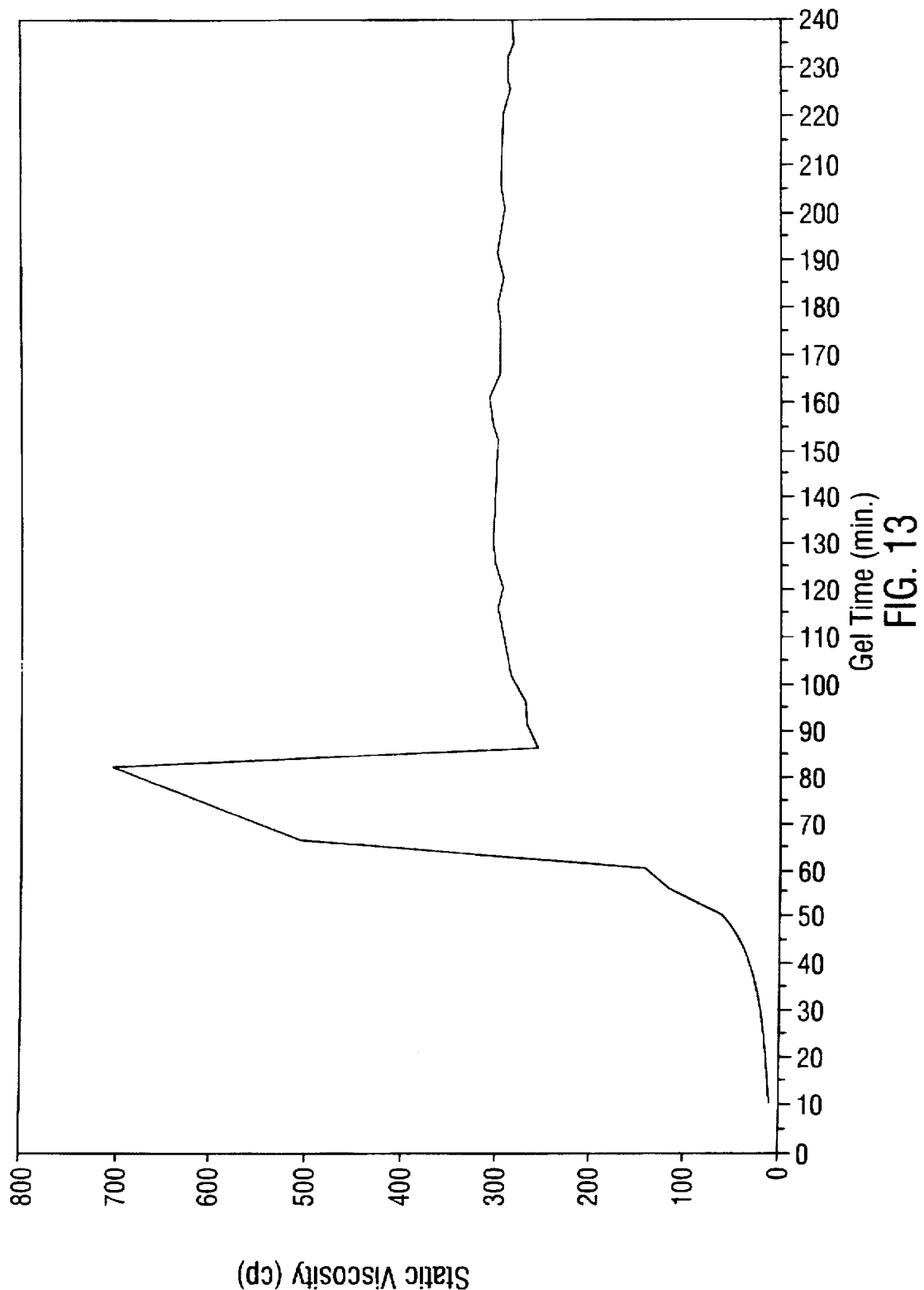
FIG. 13 illustrates analysis of gel viscosity, analyzed and plotted as ultrasonic transit time versus gel time.

FIG. 13 demonstrates analysis by a preferred embodiment of this invention of gel viscosity, analyzed and plotted as static viscosity with unity of centipoise (cp) versus gel time. The data indicates a definite increase in gel viscosity from about 100 cp to about 700 cp in about 80 minutes and a dramatic break (e.g., decreased) after about 80 minutes. Determining gel breaking time at simulated down-hole conditions of pressure and temperature is important to the oil and gas industry.

EXAMPLE 9

EXPONENTIAL GEL CROSS-LINKING DETERMINATION BASED ON DMA VISCOSITY ANALYSIS

Figure 15:
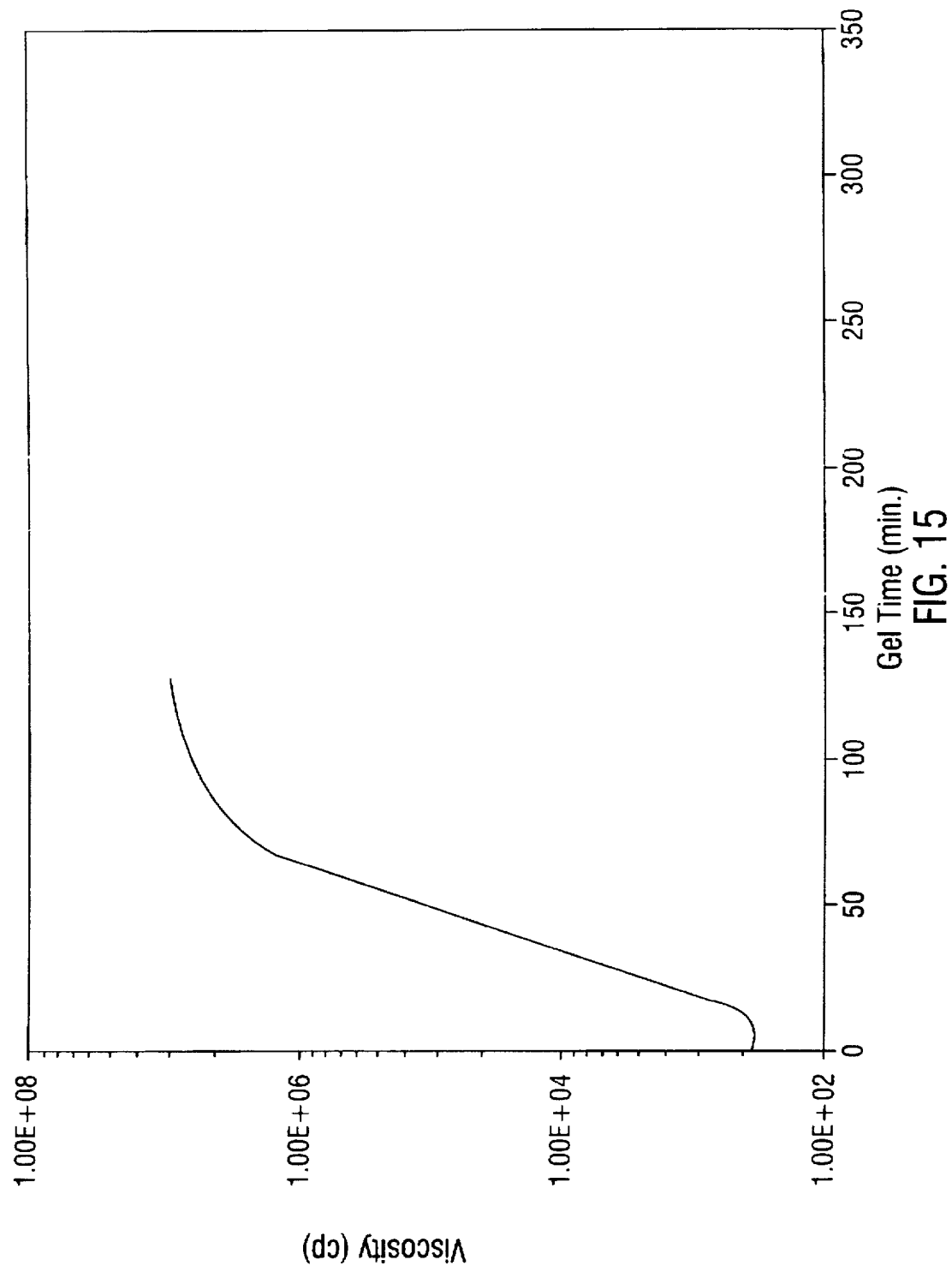
FIG. 15 illustrates analysis of an exponential increase in gel viscosity plotted as viscosity in cp versus gel time in minutes.

FIG. 15 demonstrates analysis by an embodiment of this invention of an exponential increase in gel viscosity, analyzed and plotted as gel viscosity in cp versus gel time. The data indicated a definite increase in gel viscosity from about 200 cp to about $3 \times 10^6$ cp in about 125 minutes. In this graph the data points are shown and plotted every minute as the gel strength increases. The gel used in the test is an example of a blocking gel used in completion operations on oil and gas wells. The rapid increase in gel strength can be used to block easing perforations and prevent fluid flow into the formation.

The principle of the preferred embodiments of this invention and the best mode contemplated for applying that principle have been described. It is to be understood that the foregoing is illustrative only and that other means and techniques can be employed without departing from the true scope of the invention defined in the following claims.

What is claimed is:

1. A method for simulating a sample of cement contained within a well in a subterranean formation, comprising:

maintaining the sample in a housing having walls including a wall variable in position to vary the housing length and volume in response to expansion or contraction of the sample;

controlling the temperature and pressure of the sample at the temperature and pressure prevailing within the well;

transmitting an ultrasonic signal through the sample length following such expansion or contraction;

detecting the ultrasonic signal subsequent to its transit through the sample length;

measuring and recording the time required for the signal to transit the sample length;

measuring and recording any changes in the sample length through which the ultrasonic signal passes; and determining the ultrasonic velocity of the ultrasonic signal by a predetermined relationship of ultrasonic velocity with the transit time of the ultrasonic signal and the measurement of the length of the sample through which the ultrasonic signal passes; and 5,741,971

13 non-destructively characterizing the changes in one or more certain parameters over a period of time and relative to the temperature and pressure within the well, said parameters including the density, viscosity, degree of cement slurry thickening, cement shrinkage or expansion, cement compressive strength, and dynamic Young's Modulus, from predetermined relationships between the above-listed parameters with the measurements of the ultrasonic signal transit time and the measurements of the sample lengths through which the ultrasonic signals pass.

2. A method for simulating a sample of gel contained within a well in a subterranean formation, comprising:

maintaining the sample in a housing having walls including a wall variable in position to vary the housing length and volume in response to expansion or contraction of the sample;

controlling the temperature and pressure of the sample at the temperature and pressure prevailing within the well;

transmitting an ultrasonic signal through the sample length following such expansion or contraction;

detecting the ultrasonic signal subsequent to its transit through the sample length;

measuring and recording the time required for the signal to transit the sample length;

measuring and recording any changes in the sample length through which the ultrasonic signal passes; and determining the ultrasonic velocity of the ultrasonic signal by a predetermined relationship of ultrasonic velocity with the transit time of the ultrasonic signal and the measurement of the length of the sample through which the ultrasonic signal passes; and characterizing changes in one or more parameters of the gel over a period of time and relative to the temperature and pressure within the well, said parameters including the dynamic Young's Modulus, degree of cross-linking, breaking, viscosity, density and the time at which the gel is denatured, according to a predetermined relationship of the above-listed parameters with the measurements of ultrasonic signal transit time and the measurement of the sample lengths through which the ultrasonic signal passed over the period of time.

3. A method for evaluating the physical changes in gels or cements as they change from liquid to solid or solid to liquid while simulating the conditions in a well within a subterranean formation, comprising:

maintaining a sample in a housing means;

adjusting the size of the interior area of the housing means to accommodate an expanding or contracting sample;

controlling the temperature and pressure of the sample;

transmitting an ultrasonic signal through the sample;

detecting the ultrasonic signal after its transit through the sample;

measuring and recording the time required for the signal to transit the sample; and measuring and recording the length of the sample through which each ultrasonic signal passes.

4. A method for evaluating the physical changes in gels or cements as they change from liquid to solid or solid to liquid while simulating the conditions in a well within a subterranean formation, comprising:

maintaining a sample in a housing having walls;

controlling the temperature and pressure of the sample;

transmitting an ultrasonic signal through a sample length substantially parallel and substantially equivalent to a length of the sample housing;

14 detecting the ultrasonic signal subsequent to its transit through the length;

measuring and recording the time required for the signal to transit the length; and measuring and recording the length through which the ultrasonic signal passes.

5. A method for evaluating a gel or cement material while simulating the conditions of a well within a subterranean formation, which comprises:

placing a material of known volume in a housing which is variable along its length in response to expansion or contraction of the material;

controlling the material at a pressure and temperature simulating the pressure and temperature anticipated for the material within the well;

detecting a variation, if any, in said length of the controlled sample at a selected time; and detecting the transit time of sound along said length, as varied in length at said selected time.

6. A method as defined in claim 5 in which the detection steps are repeated at different times following said selected time.

7. A method as defined in claim 5, wherein the material comprises an aqueous slurry of cement.

8. A method as defined in claim 5, wherein the material comprises a completion fluid.

9. A method as defined in claim 5, wherein the material comprises a fracturing fluid.

10. A method as defined in claim 6, wherein said method further comprises:

determining for each detection step the velocity of sound through the sample from its length at said step and the transit time of sound along the length at said step.

11. A method as defined in claim 6, wherein the weight of the sample is known and said method further comprises:

determining for each detection step the velocity of sound through the sample from its length, at said step as varied, and the transit time of sound along the varied length at said step; and calculating the dynamic modulus of the sample.

12. A method as defined in claim 11, wherein the cement when set has a known Poisson's ratio, and wherein the method further comprises calculating the dynamic modulus from the following equations.

$$V_c = \sqrt{\frac{F(v)E_d}{\rho}}, \text{where}$$

$$F(v) = \frac{(1+v)(1-2v)}{1-v}, \text{(for solids), and}$$

$V_c$ is sonic compressional wave velocity;

v is Poisson's ratio for solids;

$E_d$ is the dynamic modulus; and $\rho$ is the density of the sample.

13. A method for evaluating the performance of a sample of material wherein the material sets up to a gel, while simulating the conditions of a well in a subterranean formation, which comprises:

placing the sample having a known volume in a housing which is variable along its length in response to expansion or contraction of the material;

controlling the sample at a pressure and temperature simulating the pressure and temperature anticipated for the material within the well;

detecting the length of the controlled sample at a series of times;

detecting the transit time of sound along the length detected at each time;

wherein the series of times continues through a first time when said transit time increases sufficiently to indicate that the material has gelled.

14. A method as defined in claim 13 wherein the series of times further continues through a second time when said transit time decreases sufficiently to indicate that the gelled material has broken.

* * * * *

UNITED STATES PATENT AND TRADEMARK OFFICE
CERTIFICATE OF CORRECTION

PATENT NO. : 5,741,971
DATED : April 21, 1998
INVENTOR(S) : Lewis L. Lacy

It is certified that error appears in the above-indentified patent and that said Letters Patent is hereby corrected as shown below:

Col. 5, line 24 — change the word "ting" to "ring."
Col. 5, line 59 — change the word "soft-ware" to "software."
Col. 6, line 45 — change the phrase "ofF(v)" to "of F(v)."
Col. 12, line 37 — change the word "easing" to "casing."

Signed and Sealed this

Twenty-seventh Day of October, 1998

Attest:

BRUCE LEHMAN

*Attesting Officer*  *Commissioner of Patents and Trademarks*